US00PP37850P2

(12) United States Plant Patent
Schoenmakers

(10) Patent No.: US PP37,850 P2
(45) Date of Patent: Nov. 24, 2026

(54) ***FITTONIA* PLANT NAMED 'KEJAPA122'**

(50) Latin Name: *Fittonia albivenis*
Varietal Denomination: KEJAPA122

(71) Applicant: Schoenmakers Tussenholding B.V., Haaren (NL)

(72) Inventor: Jan Cornelis Adrianus Maria Schoenmakers, Haaren (NL)

(73) Assignee: Schoenmakers Tussenholding B.V., Haaren (NL)

( * ) Notice: Subject to any disclaimer, the term of this patent is extended or adjusted under 35 U.S.C. 154(b) by 0 days.

(21) Appl. No.: 19/375,831

(22) Filed: Oct. 31, 2025

(51) Int. Cl.
*A01H 5/12* (2018.01)
*A01H 6/00* (2018.01)

(52) U.S. Cl.
USPC ..... Plt./373

(58) Field of Classification Search
USPC ..... Plt./373
CPC ..... A01H 5/12; A01H 5/00; A01H 6/00
See application file for complete search history.

(56) References Cited

U.S. PATENT DOCUMENTS

PP16,980 P2 * 8/2006 Schoenmakers ..... A01H 6/00
Plt./373

* cited by examiner

*Primary Examiner* — June Hwu
(74) *Attorney, Agent, or Firm* — Samuel R. McCoy, Jr.

(57) ABSTRACT

'KEJAPA122' is a new and distinctive *Fittonia* plant which is characterized by a semi-upright growth habit, an abundance of narrow ovate to lanceolate foliage with serrulate margins that are highly undulated, and an adaxial foliar surface that is colored with a bright-red-on-dark-green, webbed variegation pattern. 'KEJAPA122' shows the stability of all these characteristics from generation to generation.

2 Drawing Sheets

Latin name of the genus and species: The Latin name of the genus and species of the novel variety disclosed herein is *Fittonia albivenis*.

Variety denomination: The inventive variety of *Fittonia* disclosed herein has been given the variety denomination 'KEJAPA122'.

BACKGROUND OF THE INVENTION

Parentage: 'KEJAPA122' originated as a naturally occurring, partial-plant mutation of *Fittonia albivenis* 'Forest Flame' (U.S. Plant Pat. No. 16,897), which was discovered at a commercial greenhouse in Haaren, The Netherlands, in November of 2005. The mutation was noted for its bright-red-on-dark-green variegation, relative to 'Forest Flame' which exhibits pink-on-green variegation. The mutation was harvested from the parent plant and subsequently propagated by rooting stem cuttings. The resulting plants were then grown to a mature size in order to evaluate and confirm the uniformity and stability of the unique characteristics first observed. Upon confirmation, in November 2006, the inventor selected the claimed *Fittonia* plant 'KEJAPA122' for commercialization.

Asexual Reproduction: Asexual reproduction of 'KEJAPA122' by way of rooting stem cuttings, was first performed in November of 2005 at a commercial greenhouse in Haaren, The Netherlands. Through thirty-seven subsequent generations, the plants so produced have shown that the unique features of the instant cultivar are stable and reproduced true to type.

SUMMARY OF THE INVENTION

The cultivar 'KEJAPA122' has not been observed under all possible environmental conditions, the phenotype may vary somewhat with variations in the instant environment such as temperature, day length, and light intensity, without, however, any variance in genotype. The following characteristics have been repeatedly observed and represent the distinguishing characteristics of the new *Fittonia* cultivar 'KEJAPA122'. These traits, in combination, distinguish 'KEJAPA122' as a new and distinct cultivar.

1. *Fittonia* 'KEJAPA122' exhibits a semi-upright growth habit, with decumbent lateral branches that become stoloniferous as the plant matures; and
2. *Fittonia* 'KEJAPA122' exhibits an abundance of narrow ovate to lanceolate laminas with serrulate, highly undulated margins; and
3. *Fittonia* 'KEJAPA122' exhibits pinnate foliar venation, with reticulated lateral veins, which are red-purple on the mature adaxial surface and yellow-green to orange on the mature abaxial surface; and
4. *Fittonia* 'KEJAPA122' exhibits dark yellow-green mature foliage with a red-purple coloration broadly bordering the entire network of veins which creates a bright-red-on-green, webbed variegation pattern.

BRIEF DESCRIPTION OF THE FIGURES

The photographs were taken using conventional techniques and although colors may appear different from actual colors due to light reflectance, it is as accurate as possible by conventional photographic techniques.

BOTANICAL DESCRIPTION OF THE PLANT

Figure 1:
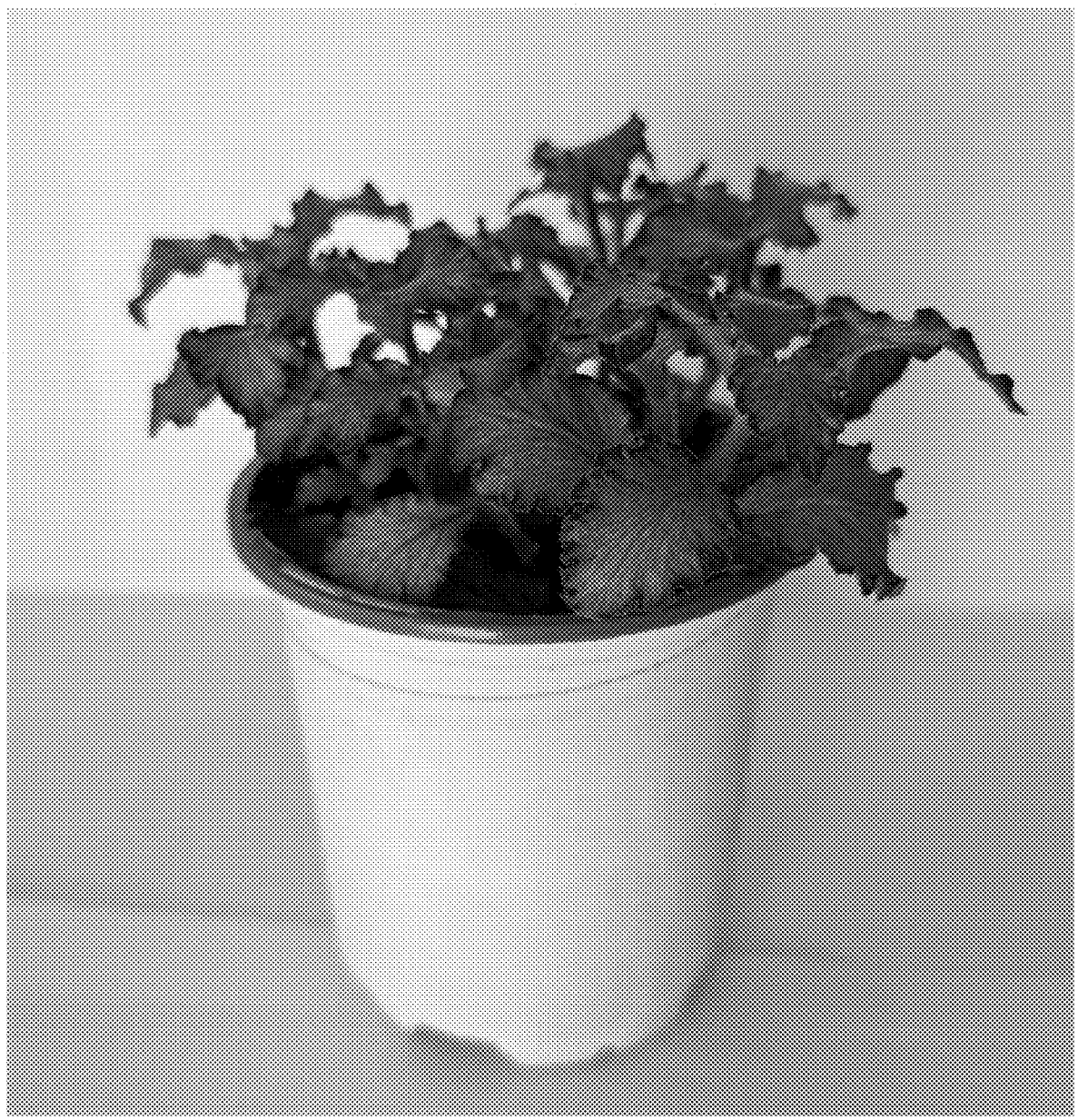
FIG. 1 shows, as nearly true as it is reasonably possible to make the same in color illustrations of this type, an exemplary plant of the new cultivar, 'KEJAPA122', approximately 14-weeks-old in a 350 mL nursery container. The plant shown was grown from a rooted cutting, potted into a nursery container, grown in a greenhouse in Stuarts Draft, Virginia.
Figure 2:
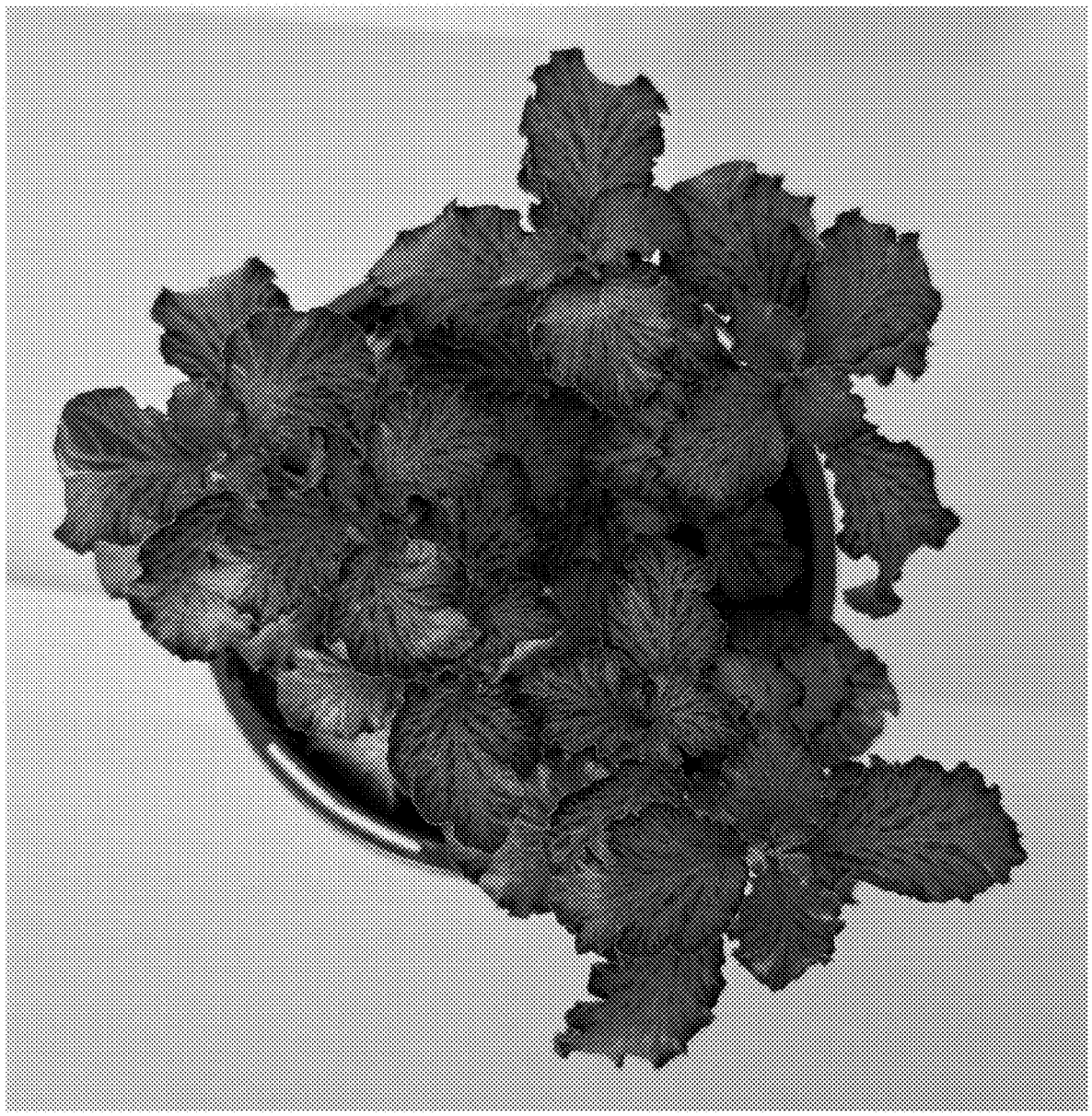
FIG. 2 illustrates the adaxial surface of the juvenile and mature foliage of the aforementioned 'KEJAPA122' plant.

The following observations and measurements were made in September of 2025. With the exception of the 51-week-old plants used to describe the stoloniferous habit of the plant, the *Fittonia* 'KEJAPA121' plants described in this botanical description are approximately 13-week-old grown in a 350 mL nursery container. Plants were produced using conventional greenhouse production protocols for *Fittonia* species which consisted of overhead irrigation once a week, grown under shade with light levels ranging from approximately 2,000 to 4,000 lumens, with ambient temperatures ranging from 20 to 35 degrees Celsius, and humidity levels ranging from 60 to 95 percent. No pest or disease measures were employed. The 51-week-old plants were grown in the same manner as the aforementioned 13-week-old plants, only they were moved to an outdoor area with rain exclusion and 30 percent shade at 30-weeks-old. These plants were manually watered as needed, and no pest or disease control measures were employed.

Those skilled in the art will appreciate that certain characteristics will vary with older or, conversely, with younger plants. 'KEJAPA122' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climatic, and cultural conditions. Color notations are based on *The Royal Horticultural Society Colour Chart*, The Royal Horticultural Society, London, Second Edition.

A botanical description of 'KEJAPA122' and comparisons with the parent plant and the most similar variety of common knowledge are provided below.

Plant description:

*Growth habit.*—Semi-upright.

*Plant form.*—Stoloniferous.

*Average height.*—5.6 cm.

*Plant spread.*—12.2 cm.

*Propagation.*— Type — Asexual propagation is accomplished by way of apical and intercalary vegetative cuttings. Time to produce a rooted cutting — Approximately 4 weeks to produce a rooted cutting. Time to produce a rooted mature plant — Approximately 14 to 20 weeks grown in a 350 mL nursery container.

*Disease resistance.*—'KEJAPA122' exhibits susceptibility in common with the parent including bacterial leaf spot caused by *Xanthomonas campestris*, fungal blight caused by *Rhizoctonia solani*, as well as common arthropod pests such as aphids, moths, fungus gnats, and thrips.

*Environmental tolerances.*—Adapt to temperatures as high as 31 degrees Celsius. Thrives in partial shade with 60-70% humidity. Leaf scorch will occur in direct sunlight. 'KEJAPA122' requires irrigation once every 5-7 days and prefers growing under 50 $\mu mol/m^2/s$ shaded light.

Root system:

*General.*—Fine branched.

*Diameter of roots.*—1.0 mm, on average.

*Texture.*—Smooth and glabrous.

*Color.*—Greyed-orange, nearest to RHS 165D.

Stem:

*General branching habit.*—Basally branching main stems; with decumbent lateral branching.

*Color of developing stems.*—Green, closest to RHS 143C.

*Color of mature stems.*—Green, closest to RHS 143C, with an overtone of greyed-purple, closest to RHS 183C.

*Color at internodes.*—Green, closest to RHS 143C.

*Texture.*—Coriaceous; trichomes present; trichomes are approximately 0.1 mm in length and colored white, RHS 155A.

*Luster.*—Slightly glossy.

*Stolons.*—Quantity — 4. Length — 6.8 cm. Diameter — 0.5 cm. Internode length — 1.8 cm. Attitude — Varying between 15 and 30 degrees from horizontal. Coss-section — Terete.

*Lateral branches.*—Quantity — 4. Length — 5.6 cm. Diameter — 0.4 cm. Internode length — 1.1 cm. Attitude — 15-degree angle from the main stems.

Foliage:

*Quantity.*—8 leaves per lateral branch.

*Arrangement.*—Opposite.

*Attachment.*—Petiolate.

*Division.*—Simple.

*Lamina.*—Shape — Narrow ovate to lanceolate. Length — 3.9 cm. Width — 1.8 cm. Apex — Narrow apiculate to aristate; leaf tip is long relative to the total length of the lamina. Base — Acute. Cross-section — Carinate. Attitude — Semi-upright. Margin — Serrulate, highly undulated. Texture and luster of the adaxial surface — Coriaceous and slightly glossy. Texture and luster of the abaxial surface — Coriaceous and matte with salient veins. Color — Juvenile foliage, adaxial surface — Yellow-green, nearest to RHS 144C, and margined darker, RHS 147A. Additionally, the entire network of veins is broadly margined with a combination of red and red-purple, a combination of RHS 46C, 53C, and 57B. This margining of the venation creates a bright-red-on-dark-green, webbed variegation pattern. Juvenile foliage, abaxial surface — Green, RHS 143C and transitioning to 143B towards the margins. Mature foliage, adaxial surface — Yellow-green, nearest to RHS 144C, and margined darker, RHS 147A. Additionally, the entire network of veins is broadly margined with a combination of red and red-purple, a combination of RHS 46C, 53C, and 57B. This margining of the venation creates a bright-red-on-dark-green, webbed variegation pattern. Mature foliage, abaxial surface — Green, RHS 143C and transitioning to 143B towards the margins. Venation — Pattern — Pinnate, with reticulated lateral veins. Color — Juvenile foliage, adaxial surface — Red, RHS 46C. Juvenile foliage, abaxial surface — Yellow-green, nearest to a blend of RHS 145B and 145C, transitioning to orange, RHS 28B, distally. Mature foliage, adaxial surface — Red-purple, RHS 63B. Mature foliage, abaxial surface — Yellow-green, nearest to a blend of RHS 145B and 145C, transitioning to orange, RHS 28B, distally.

*Petiole*.—Length — 1.0 cm. Diameter — 0.1 cm. Texture — Smooth; glabrous. Luster — Very slightly glossy. Color, adaxial surface — Green, closest to RHS 143C, and suffused with greyed-purple, RHS 183C. Color, abaxial surface — Green, closest to RHS 143C, and suffused with greyed-purple proximally, RHS 183C.

Inflorescence: No flowering has been observed to date.

COMPARISONS WITH THE PARENT PLANTS

Plants of the new cultivar 'KEJAPA122' may be distinguished from the parent plant, *Fittonia albivenis* 'Forest Flame' (U.S. Plant Pat. No. 16,897), by the characteristics described in Table 1.

TABLE 1

Comparison between 'KEJAPA122' and 'Forest Flame'.

| Characteristic | 'KEJAPA122' | 'Forest Flame' |
|---|---|---|
| Leaf shape. | Narrow ovate to lanceolate leaves with narrow apiculate to aristate apices and acute bases. | Narrow elliptic leaves with broad acute to rounded apices and attenuate bases. |
| Leaf margins. | Serrulate, highly undulated. | Entire, considerably wavy. |
| General coloration of the adaxial surface of mature foliage. | Dark yellow-green with a red-purple coloration broadly bordering the entire network of veins which creates a bright-red-on-dark-green, webbed variegation pattern. | A lighter shade of yellow-green relative to 'KEJAPA122', with the venation margined with pink, which creates a pink-on-green, webbed variegation pattern. |
| Venation color, adaxial surface. | Red, becoming red-purple as the foliage matures. | The midrib is greyed-purple; lateral veins are red. |

COMPARISONS WITH THE MOST SIMILAR COMMERCIAL VARIETY

Plants of the new cultivar 'KEJAPA122' may be distinguished from the most similar commercial comparator known to the inventor, *Fittonia albivenis* 'Joly Josan' (U.S. Plant Pat. No. 16,980), by the characteristics described in Table 2.

TABLE 2

Comparison between 'KEJAPA122' and 'Joly Josan'.

| Characteristic | 'KEJAPA122' | 'Joly Josan' |
|---|---|---|
| Abundance of foliage. | Average of 8 leaves per lateral branch. | Average of 4 leaves per lateral branch. |
| Leaf shape. | Narrow ovate to lanceolate leaves with narrow apiculate to aristate apices and acute bases. | Elliptical leaves with rounded apices and attenuate bases. |
| Leaf margins. | Serrulate, highly undulated. | Entire to repand. |
| General coloration of the adaxial surface of mature foliage. | Dark yellow-green with a red-purple coloration broadly bordering the entire network of veins which creates a bright-red-on-dark-green, webbed variegation pattern. | Lighter yellow-green relative to 'KEJAPA122', with a red-purple coloration that more narrowly borders the pinnate network of veins which creates a red-on-green, pinnate variegation pattern. |
| Venation color, adaxial surface. | Red, becoming red-purple as the foliage matures. | Red. |

That which is claimed is:

1. A new and distinct variety of *Fittonia* plant named 'KEJAPA122', substantially as described and illustrated herein.

* * * * *